(12) United States Patent
Park et al.

(10) Patent No.: US 9,956,354 B2
(45) Date of Patent: May 1, 2018

(54) NOZZLE DEVICE AND MINIMALLY INVASIVE INJECTION DEVICE COMPRISING SAME

(71) Applicant: AMOREPACIFIC CORPORATION, Seoul (KR)

(72) Inventors: Jin Woo Park, Yongin-si (KR); Min Kyoung Kwon, Yongin-si (KR); Ji Hye Jang, Yongin-si (KR); Joon Ho Bae, Yongin-si (KR); Jin Kyu Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 572 days.

(21) Appl. No.: 14/412,935

(22) PCT Filed: Jul. 12, 2013

(86) PCT No.: PCT/KR2013/006270
§ 371 (c)(1),
(2) Date: Jan. 5, 2015

(87) PCT Pub. No.: WO2014/014239
PCT Pub. Date: Jan. 23, 2014

(65) Prior Publication Data
US 2015/0157809 A1    Jun. 11, 2015

(30) Foreign Application Priority Data
Jul. 19, 2012    (KR) .................. 10-2012-0078921

(51) Int. Cl.
*A61M 5/32*    (2006.01)
*A61M 5/20*    (2006.01)
(Continued)

(52) U.S. Cl.
CPC ............ *A61M 5/3298* (2013.01); *A61M 5/20* (2013.01); *A61M 5/204* (2013.01);
(Continued)

(58) Field of Classification Search
CPC ............ A61M 37/0076; A61M 3/0275; A61M 5/3298; A61M 5/204; A61M 4/46; A61M 2037/0023; A61M 5/50; A61M 2037/003
See application file for complete search history.

(56) References Cited

U.S. PATENT DOCUMENTS 4,671,277 A * 6/1987 Beuchat ............ A61M 37/0076
606/185
6,334,856 B1 * 1/2002 Allen ................ A61B 5/14514
128/898

(Continued)

FOREIGN PATENT DOCUMENTS

| CN | 101979108 | 2/2011 |
| JP | 200744529 | 2/2007 |

(Continued)

OTHER PUBLICATIONS

International Search Report-PCT/KR2013/006270 dated Oct. 28, 2013.

(Continued)

*Primary Examiner* — Nathan R Price
*Assistant Examiner* — Melissa A Snyder
(74) *Attorney, Agent, or Firm* — Cantor Colburn LLP (57) ABSTRACT

Disclosed is a nozzle device and a minimally invasive injection device, and the nozzle device for a minimally invasive injection device according to an exemplary embodiment includes an outlet to generate a microjet of a liquid, and an injection part of a micro-scale size connected to the outlet and adapted to be inserted into a skin tissue to a preset depth.

13 Claims, 7 Drawing Sheets

(51) Int. Cl.
*A61M 5/315* (2006.01)
*A61M 5/46* (2006.01)
*A61M 37/00* (2006.01)
*A61M 5/30* (2006.01)

(52) U.S. Cl.
CPC .......... *A61M 5/31511* (2013.01); *A61M 5/46* (2013.01); *A61M 37/0015* (2013.01); *A61M 5/2053* (2013.01); *A61M 5/30* (2013.01); *A61M 2037/003* (2013.01); *A61M 2037/0023* (2013.01)

(56) References Cited

U.S. PATENT DOCUMENTS

| | | | |
|---|---|---|---|
| 7,942,845 | B2 | 5/2011 | Williamson et al. |
| 8,066,662 | B2 | 11/2011 | Azar et al. |
| 2003/0050602 | A1 | 3/2003 | Pettis et al. |
| 2003/0181863 | A1* | 9/2003 | Ackley ............. A61M 37/0015 604/201 |
| 2004/0116953 | A1* | 6/2004 | Dixon ............... A61M 37/0076 606/186 |
| 2005/0010236 | A1* | 1/2005 | Frister ............... A61M 37/0076 606/116 |
| 2005/0154347 | A1 | 7/2005 | Neracher |
| 2005/0209566 | A1 | 9/2005 | Yeshurun et al. |
| 2006/0027285 | A1 | 2/2006 | Neracher |
| 2007/0055200 | A1 | 3/2007 | Gilbert |
| 2007/0055214 | A1 | 3/2007 | Gilbert |
| 2009/0054842 | A1 | 2/2009 | Yeshurun et al. |
| 2011/0015567 | A1 | 1/2011 | Azar et al. |

FOREIGN PATENT DOCUMENTS

| | | |
|---|---|---|
| KR | 100888831 | 3/2009 |
| KR | 1020110013796 | 2/2011 |
| KR | 101062022 | 9/2011 |
| RU | 2438719 | 1/2012 |
| WO | 2005049107 | 6/2005 |
| WO | 2007115039 | 10/2007 |
| WO | 2009091099 | 7/2009 |
| WO | 2010016049 | 2/2010 |
| WO | 2010067345 | 6/2010 |

OTHER PUBLICATIONS

Written Opinion—PCT/KR2013/006270 dated Oct. 28, 2013.
Chinese Office Action—Chinese Application No. 201380038500.8 dated Jun. 8, 2017.
Chinese Office Action—Chinese Application No. 201380038500.8 dated Sep. 5, 2016.
Extended European Search Report (EESR)—European Application No. 13819913.8 dated Mar. 17, 2015.
Russia Office Action—Russian Application No. 2015103600 dated Jun. 20, 2017.
Japanese Office Action—Japanese Application No. 2015-523002 dated Jul. 21, 2017.

* cited by examiner

NOZZLE DEVICE AND MINIMALLY INVASIVE INJECTION DEVICE COMPRISING SAME

TECHNICAL FIELD

The present disclosure relates to a nozzle device and a minimally invasive injection device, and more particularly, to a nozzle device that may minimize pain and bleeding from a skin while minimizing an injection loss of a liquid and a minimally invasive injection device.

BACKGROUND ART

In medical and cosmetic procedures, there is a need to inject a liquid under the surface of the skin. For example, injecting insulin under the surface of the skin or injecting a substance such as collagen under the surface of the skin for cosmetic purposes is the case.

A most common method for injecting a liquid includes inserting an injection needle into a desired part to a desired depth. However, when an injection needle is used, pain and bleeding are involved, and an injection needle may be inserted improperly or wrongly based on a skill level of a user. Also, in the event of improper insertion into the skin, severe damage may occur to a skin tissue and the damaged skin needs treatment for a considerable period of time.

Accordingly, to solve the problem, a needle-free syringe has been recently developed. Examples of a needle-free syringe include U.S. Pat. No. 8,066,662, U.S. Pat. No. 7,942,845, Korean Patent No. 10-1062022, WO2010/067345, and WO2010/016049.

A needle-free syringe does not have an injection needle, and instead, ejects a liquid in the form of a high pressure microjet to allow the liquid to permeate into the skin in the form of the microjet. However, in the case of this syringe, to allow the microjet to penetrate and permeate into the skin to a desired depth, sufficient pressure and velocity needs to be guaranteed, and the microjet permeated into the skin needs to be immediately diffused into the tissue. However, the skin varies, for each layer, particularly, the stratum corneum and the epidermis, in thickness, elasticity, flexibility and hardness, and even in the same individual, varies in each part.

Thus, a needle-free syringe is very difficult to uniformly permeate a liquid, and because while permeating, an angle and a distance between a skin surface and an orifice from which a microjet is ejected and properties of a medicinal fluid to be permeated have a significant influence on an amount and a depth being permeated, controlling a loss and a permeation depth during injection of the medicinal fluid is difficult. Particularly, when a medicinal fluid of high viscosity is to be delivered, phenomena occurs in which a microjet of sufficient velocity is not generated and some of the permeated microjet is not diffused into the skin and comes out of the skin and collides backwards with a subsequent microjet emitted from an orifice, thereby further reducing the microjet velocity, resulting in further reduction in skin permeation capability.

SUMMARY OF INVENTION

Technical Problem

To address the above issues, the present disclosure is directed to providing a minimally invasive injection device which may minimize an injection loss ratio of a microjet while minimizing pain and bleeding from a skin when permeated into the skin.

Also, the present disclosure is directed to providing a minimally invasive injection device which may uniformly deliver a liquid without a loss, independent of properties of the liquid and characteristics of a target skin.

Technical Solution

A nozzle device for a minimally invasive injection device according to an exemplary embodiment of the present disclosure includes an outlet to generate a microjet of a liquid, and an injection part of a micro-scale size connected to the outlet and adapted to be inserted into a skin tissue to a preset depth.

The outlet may be detachably connected to a first reservoir part containing the liquid to be injected.

The outlet and the first reservoir part may have locking structures, respectively, to be locking-engaged with each other.

A minimum diameter of the outlet may be less than or equal to 0.5 mm.

An inner diameter of the injection part may be from 50 to 450 μm.

The injection part may be inserted into the skin issue to the depth between 0.1 and 20 mm.

A minimally invasive injection device according to an exemplary embodiment of the present disclosure includes a nozzle part including a first reservoir part to contain a liquid to be injected, an outlet to generate a microjet of the liquid, and an injection part of a micro-scale size connected to the outlet and adapted to be inserted into a skin tissue to a preset depth, and a pressure providing part including a first pressure applying part connected to the first reservoir part and configured to apply pressure to the liquid, and a first pressure generator to provide the pressure to the first pressure applying part.

The minimally invasive injection device may further include a liquid providing part of manual or automated type connected to the first reservoir part and configured to provide the liquid of a preset amount.

The outlet may be detachably connected to the first reservoir part containing the liquid to be injected.

The outlet and the first reservoir part may have locking structures, respectively, to be locking-engaged with each other.

A single dose ejectable from the first reservoir part may be from 1 to 1000 μl.

The liquid providing part of automated type may include a second reservoir part to store the liquid to be injected, a second pressure applying part to apply pressure to the second reservoir part, and a second pressure generator to provide the pressure to the second pressure applying part.

The minimally invasive injection device may further include a controller connected to the second pressure generator and configured to control a movement distance of the second pressure generator.

The minimally invasive injection device may further include a third pressure applying part connected to the first pressure applying part and configured to apply the pressure to the first reservoir part.

The minimally invasive injection device may further include a controller connected to the first pressure generator and configured to control at least one of a magnitude and a generation time of the pressure generated by the first pressure generator.

The controller may be connected to the first pressure generator and configured to control an extended distance or a retracted distance of the first pressure applying part.

The controller may be connected to the first pressure generator and configured to control to continuously move the first pressure applying part forward or repeatedly move the first pressure applying part forward and backward.

A jet force of the microject being jet may be adjusted by adjusting a diameter of the outlet.

A minimum diameter of the outlet may be less than or equal to 0.5 mm.

An inner diameter of the injection part may be from 50 to 450 μm.

The injection part may be inserted into the skin issue to the depth between 0.1 and 20 mm.

The first pressure generator or the second pressure generator may be any one of the group consisting of a compression spring, compressed gas, an explosive chemical substance, piezoelectricity, an electric driving motor, a linear Lorentz's force driving motor, an electric cylinder, and a linear motion guide.

The first pressure generator and the second pressure generator may be an integral pressure generator connected to the first pressure applying part and the second pressure applying part.

A plurality of outlets and injection parts connected to the outlets may be connected to the first reservoir part, and an area in which the plurality of outlets and injection parts connected to the outlets are placed may be adjusted to adjust an ejection area of the microjet.

The first pressure generator or the second pressure generator may be adapted to generate the pressure from 1 to 100 bar.

The liquid may include at least one selected from the group consisting of hyaluronic acid, collagen, a stem cell, a stem cell culture fluid, a fat cell, fat, silicon, vitamin, a placenta extract, blood plasma, tranexamic acid, a saline solution, polyvinyl alcohol, poly(methyl methacrylate), polyethylene glycol, cross-linked hyaluronic acid, calcium hydroxy apatide, polylactic acid, poly(lactic-co-glycolic acid), pteroylglutamic acid, poly-gamma-glutamic acid, phospholipid, deoxycholic acid, minoxidil, finasteride, dutasteride, a growth factor, botulinum toxin, alginic acid, chitosan, chondroitin sulfate, dermatan sulfate, hyaluronate lyase, an antibody, a pain relief ingredient, and an anesthetic ingredient.

The liquid may be provided as at least one of a solution, a suspension, and a dispersion in which particles including active ingredients are dispersed.

Advantageous Effects

According to an exemplary embodiment of the present disclosure, there is provided a minimally invasive injection device that may mitigate discomfort of a patient caused by pain and bleeding while minimizing an injection loss ratio under a skin when a microjet is permeated into the skin.

Also, there is provided a minimally invasive injection device that may deliver a uniform amount of liquid to a uniform depth independent of skin characteristics of an individual when injecting a liquid including active ingredients of various properties.

Also, there is provided a minimally invasive injection device that may allow continuous injection to increase an injection area for one-time injection or perform procedures on many objects.

BEST MODE

Hereinafter, a detailed description of a minimally invasive injection device according to various exemplary embodiments of the present disclosure is provided with reference to FIGS. 1 through 6.

Figure 1:
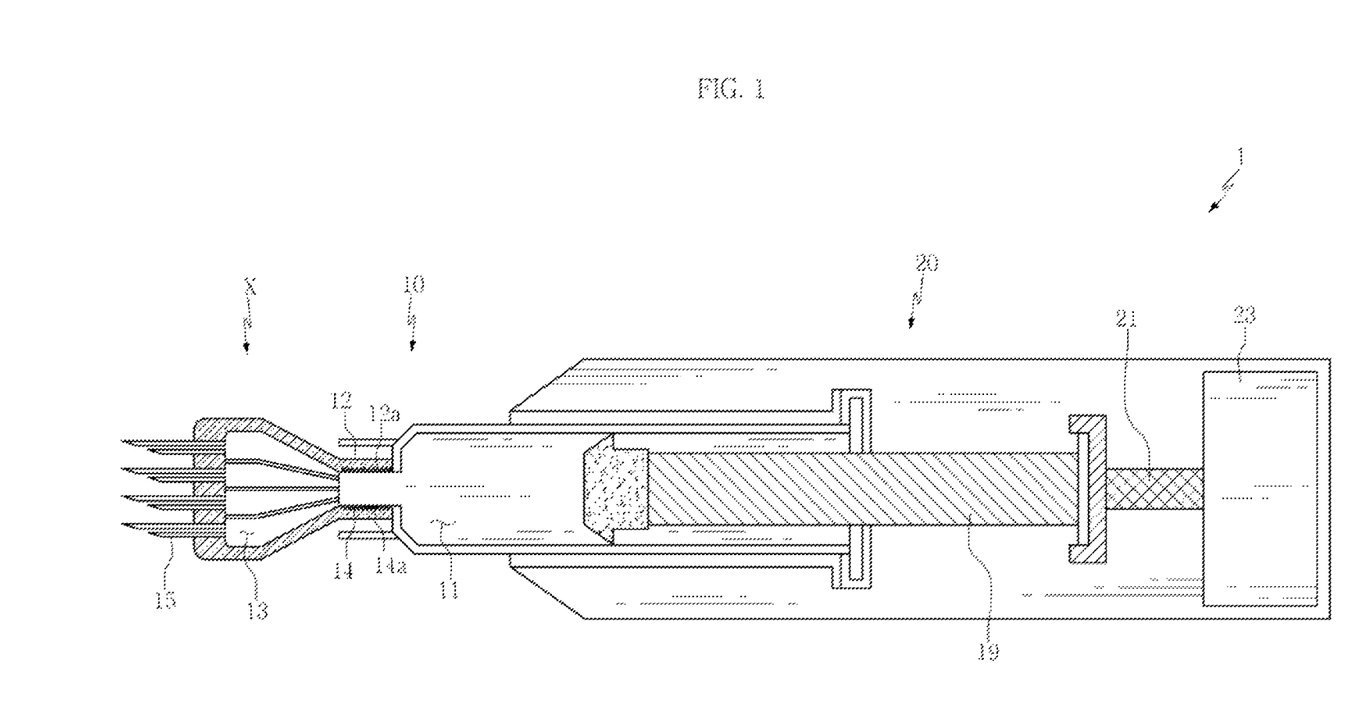
FIG. 1 is a schematic diagram illustrating a minimally invasive injection device according to an exemplary embodiment of the present disclosure.

FIG. 1 is a schematic diagram illustrating a minimally invasive injection device according to an exemplary embodiment of the present disclosure.

Referring to FIG. 1, the minimally invasive injection device 1 according to an exemplary embodiment of the present disclosure includes a nozzle part 10 (hereinafter, also referred to as a 'nozzle device') and a pressure providing part 20.

The nozzle part 10 according to an exemplary embodiment of the present disclosure includes an outlet 13 to generate a microjet, and an injection part 15 of a micro-scale size connected to the outlet 13 and adapted to be inserted into a skin tissue to a preset depth.

The outlet 13, or an orifice may be adapted to have a desired size in diameter to generate a microjet of a desired liquid.

According to an exemplary embodiment of the present disclosure, a jet force of the microjet may be adjusted by adjusting the diameter of the outlet 13. Because the diameter of the outlet 13 is inversely proportional to the jet force of the microjet, the jet force of the microjet may be adjusted by adjusting the diameter of the outlet 13 based on a part and a property of a target skin or tissue.

According to an exemplary embodiment of the present disclosure, a minimum diameter of the outlet 13 may be less than or equal to 0.5 mm. Particularly, the minimum diameter of the outlet 13 may be less than or equal to 0.3 mm, preferably, 0.2 mm. This is to permeate the liquid into a desired skin tissue quickly under pressure within the nozzle part 10.

According to an exemplary embodiment of the present disclosure, an area being jetted may be adjusted. More specifically, an injection area may be adjusted by placing a plurality of injection parts 15 within a preset area to adjust the injection area of the microjet. When one injection needle is used according to a related art, a liquid is injected into only one spot with one-time injection, but when the nozzle part according to an exemplary embodiment of the present disclosure is used, because the plurality of injection parts 15 is placed over a predetermined area, a liquid may be injected into a plurality of spots over a desired area of a skin of an object. Thus, the minimally invasive injection device may inject a liquid with one-time injection over a desired area with no need to inject multiple times.

The injection part 15 is configured to inject a liquid filled in a first reservoir part 11 into a target skin tissue. The microjet emitted through the outlet 13 may be guided to a preset skin depth by the desired injection part 15. According to an exemplary embodiment of the present disclosure, a needle of a micro-scale size may be used as the injection part 15.

According to an exemplary embodiment of the present disclosure, before injection, the injection part 15 may come into contact with the skin, penetrate through the stratum corneum or the epidermis, and be located on the dermis. Then, a high speed and high pressure microjet may be ejected into and below the dermis at a high speed, penetrate into a target part, and be diffused and absorbed into a surrounding tissue.

In the case of a traditional needle-free device, because a microjet enters the stratum corneum or the epidermis directly, the microjet does not permeate into and below the dermis. Moreover, the presence of a microject not penetrating the stratum corneum or the epidermis and coming out of them reduces efficiency of a minimally invasive injection device. However, according to an exemplary embodiment of the present disclosure, because the injection part 15 guides the microjet to the stratum corneum or the epidermis, the microjet may go through the stratum corneum or the epidermis safely and be injected to a desired depth. Particularly, the stratum corneum and the epidermis differ in thickness and hardness for each individual and for each part of an individual, but according to an exemplary embodiment of the present disclosure, because the microjet is guided to the stratum corneum and the epidermis by the injection part 15, the microjet may be injected into and below the dermis in a simple manner without a separate operation of adjusting the velocity and pressure of the microjet.

Also, when a traditional syringe is used, it is difficult to adjust an insertion depth of a needle, and due to a hole created in the skin by the needle, an object feels pain and in some instances, bleeds, and a liquid flows out through the needle hole created in the skin, leading to a liquid loss, but according to an exemplary embodiment of the present disclosure, the injection part 15 penetrates the skin to a minimum extent, and thus, an object scarcely suffers from bleeding and pain and a liquid loss caused by a liquid outflow is prevented.

An insertion depth of the injection part 15 according to an exemplary embodiment of the present disclosure may be from 0.1 to 20 mm. When the insertion depth is less than 0.1 mm, it is difficult to guide through the stratum corneum or the epidermis, and when the insertion depth exceeds 20 mm, an object may feel pain.

Preferably, based on a location and a skin thickness of a target part, the insertion depth of the injection part 15 may be from 0.5 to 10 mm and from 0.2 to 5 mm.

According to an exemplary embodiment of the present disclosure, an inner diameter of the injection part 15 may be from 50 to 450 µm. When the inner diameter is less than 50 µm, it is difficult to generate a microjet, and when the inner diameter exceeds 450 µm, a liquid may come out or bleeding may occur.

Preferably, the inner diameter of the injection part 15 may be from 50 to 410 µm, from 50 to 220 µm, and from 50 to 170 µm, based on properties of a target liquid such as viscosity or a target part.

According to an exemplary embodiment of the present disclosure, the nozzle part 10 may further include the first reservoir part 11 to store a liquid corresponding to a single dose. Also, the first reservoir part 11 may be constructed as a syringe or its similar form of housing, and may be configured to store an amount of liquid corresponding to an intended number of injections.

The first reservoir part 11 may be connected to a liquid providing part which provides a liquid. According to an exemplary embodiment of the present disclosure, the first reservoir part 11 may be integrally formed with the liquid providing part so that a single dose or more of liquid may be stored in the first reservoir part 11 and ejected one or more times. However, the present disclosure is not necessarily limited thereto, and according to another exemplary embodiment of the present disclosure, a separate liquid providing part of manual or automated type which provides a preset amount of liquid, for example, a liquid corresponding to a single dose, may be included.

According to an exemplary embodiment of the present disclosure, a single dose injectable through the first reservoir part 11 may be from 1 to 1000 µl. The present disclosure is not necessarily limited thereto, and it is obvious that the single dose may be variously selected as desired.

Referring to FIG. 1, the outlet 13 may be detachably connected to the first reservoir part 11 containing the liquid to be injected.

The outlet 13 may include a first connecting part 12 which is connected to the first reservoir part 11, and the first connecting part 12 may have a locking structure 12a for locking engagement with the first reservoir part. Also, the first reservoir part 11 may include a second connecting part 14 which is connected to the outlet 13, and the second connecting part 14 may have a locking structure 14a for locking engagement with the outlet 13.

As the first connecting part 12 and the second connecting part 14 have the locking structures 12a and 14a shaped of screw threads to be engaged with each other, respectively, the outlet 13 and the first reservoir part 11 may be thread engaged.

Thus, a needle part X including the outlet 13 and the injection part 15 may be detachably connected to the first reservoir part 11, and by coupling the outlet 13 and the injection part 15 to the first reservoir part 11, the nozzle part 10 may be constructed.

Accordingly, because a user needs to replace only the needle part X in the nozzle part 10, the user may reduce efforts to change the injection device each time an object is changed and save the maintenance and replacement costs. Also, the user may use the injection device more sanitarily by replacing the needle part X as needed.

According to an exemplary embodiment of the present disclosure, a third pressure applying part 19 which applies the pressure to the first reservoir part 11 may be further included. The third pressure applying part 19 may be, but not necessarily limited to, a plunger.

The third pressure applying part 19 is connected to the pressure providing part 20, to be concrete, a first pressure applying part 21, and is configured to transmit the pressure provided by the pressure providing part 20 to the first reservoir part 11.

The pressure providing part 20 is configured to provide the pressure to allow the nozzle part 10 to generate a microjet. The pressure providing part 20 includes the first pressure applying part 21 and a first pressure generator 23.

The first pressure applying part 21 may be a piston adapted to make a linear motion within the pressure providing part 20 or a housing of the minimally invasive injection device.

The first pressure generator 23 corresponds to a device for providing the pressure to the first pressure applying part 21, and may be configured to provide the pressure by various methods in the art, for example, a motor type, an air pressure type, or a gas emission type.

The first pressure generator 23 may be placed in one housing together with the first pressure applying part 21, but the present disclosure is not necessarily limited thereto, and the first pressure generator 23 may be placed outside of a housing in which the first pressure applying part 21 is placed, within the range of providing the pressure to the first pressure applying part 21.

The first pressure generator 23 enables the first pressure applying part 21 to make an instantaneous high-speed linear motion, and when the first pressure applying part 21 moves forward instantaneously at a high speed within the pressure providing part 20, the pressure may be applied to the liquid present in the first reservoir part 11 of the nozzle part 10 directly through the first pressure applying part 21 or indirectly through the third pressure applying part 19.

According to an exemplary embodiment of the present disclosure, the first pressure generator 23 may further include a controller (not shown) to control at least one of a magnitude and a generation time of the pressure generated by the first pressure generator 23. That is, the controller is configured to allow a user to adjust an amount of energy generated by the first pressure generator 23 through the controller, and particularly, the controller is configured to adjust a permeation depth of the microjet, for example, to a depth sufficient for the microjet to permeate into and below the dermis by adjusting the strength of the pressure, and adjust a jet amount by adjusting the pressure generation time.

According to an exemplary embodiment of the present disclosure, it is obvious that a transparent window through which a storage amount of the first reservoir part 11 is seen may be configured to observe an amount of liquid being injected.

The third pressure applying part 19 may be located in a retracted position at a liquid filling location, and in an extended position at a liquid ejection location. A one-time extended distance is proportional to a single dose. Thus, according to an exemplary embodiment of the present disclosure, the controller (not shown) may be configured to adjust a single dose by adjusting the pressure generated by the pressure providing part 20 to adjust a one-time extended distance.

According to an exemplary embodiment of the present disclosure, the first pressure generator 23 may include, but not necessarily limited to, any one of the group consisting of a compression spring, compressed gas, an explosive chemical substance, piezoelectricity, an electric driving motor, a linear Lorentz's force driving motor, an electric cylinder, and a linear motion guide, and various pressure generators in the art may be applied.

Figure 2:
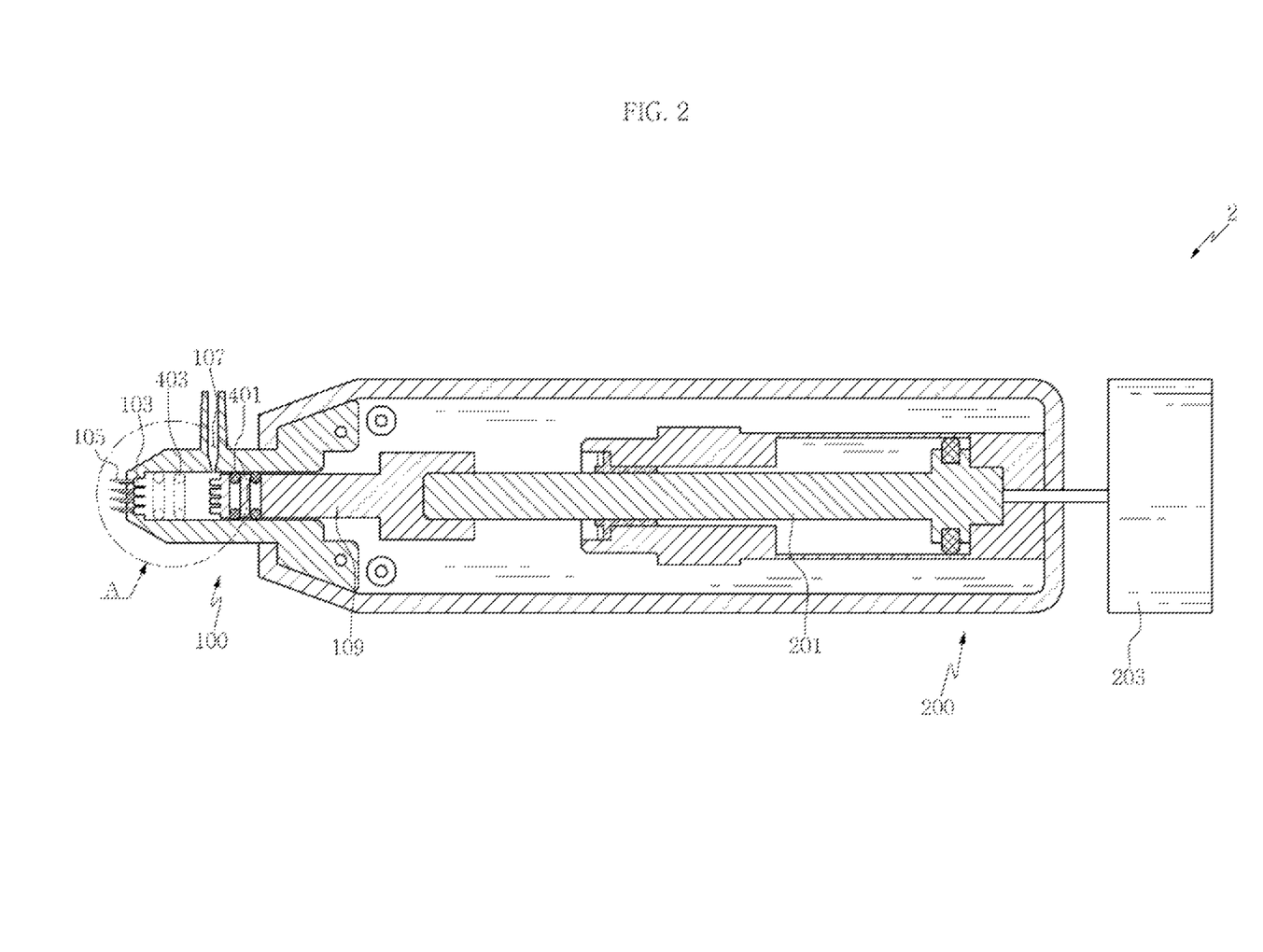
FIG. 2 is a schematic diagram illustrating a minimally invasive injection device according to a second exemplary embodiment of the present disclosure.
Figure 3A:
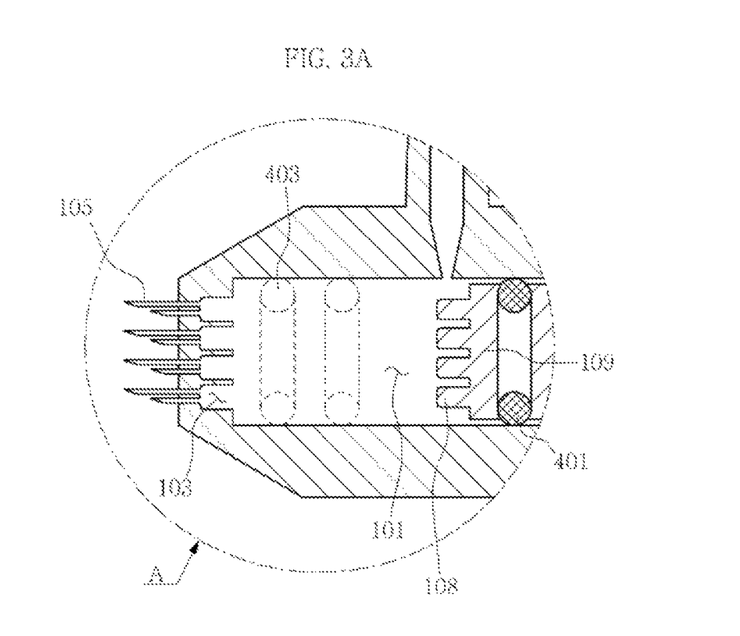
FIGS. 3A through 3C are partially enlarged views illustrating various exemplary embodiments of section A of FIG. 2.
Figure 3B:
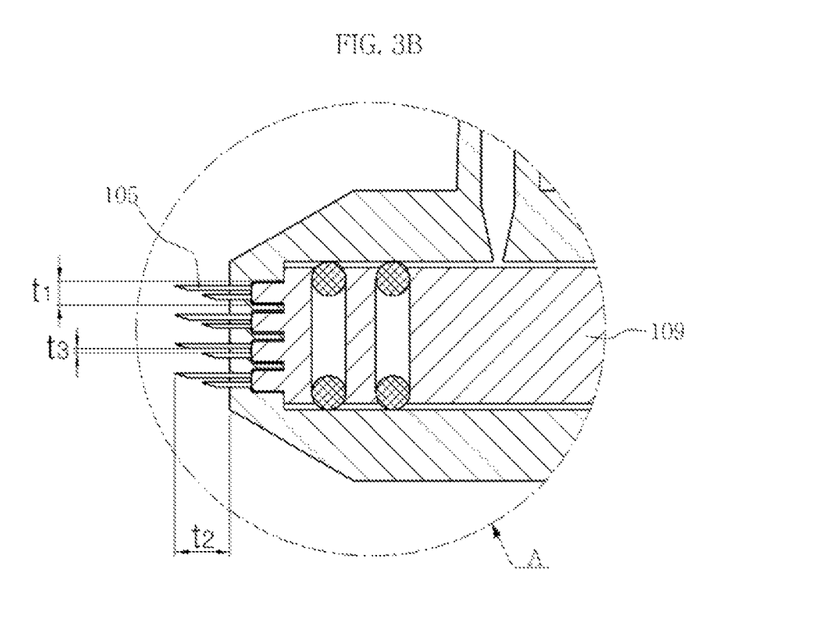
Figure 3C:
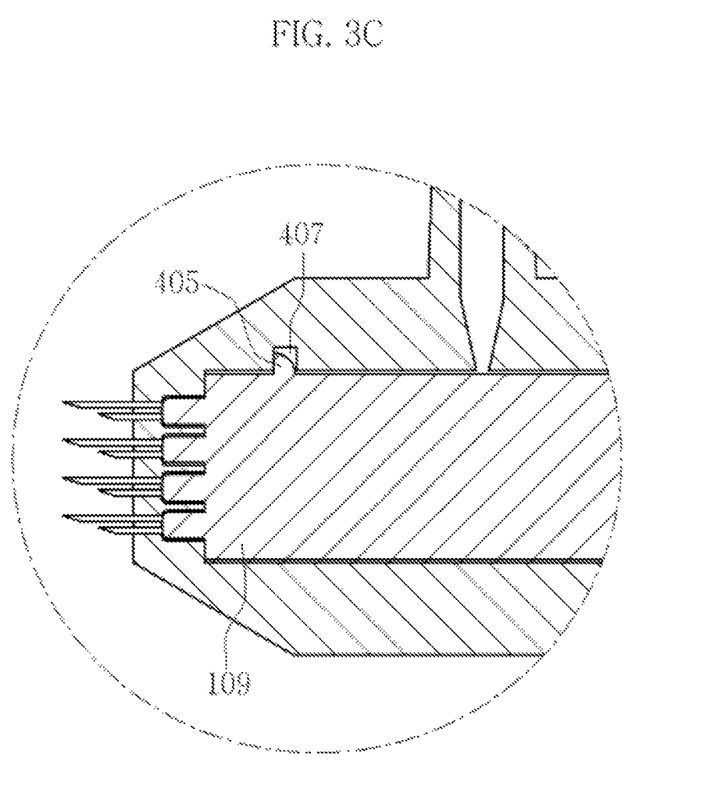

FIG. 2 is a schematic diagram illustrating a minimally invasive injection device according to a second embodiment of the present disclosure. FIG. 3A is a partially enlarged view of section A of FIG. 2 illustrating a state that a liquid is filled in a nozzle part 100, FIG. 3B is a partially enlarged view of section A of FIG. 2 illustrating a state that the liquid is ejected from the nozzle part 100, and FIG. 3C is a partially enlarged view of the nozzle part 100 according to another exemplary embodiment of the present disclosure.

Referring to FIGS. 2 and 3A, the minimally invasive injection device 2 according to the second exemplary embodiment of the present disclosure provides the nozzle part 100 and a pressure providing part 200 integrally formed.

In the minimally invasive injection device according to an exemplary embodiment of the present disclosure, the nozzle part 100 includes a first reservoir part 101 in which a liquid to be injected is received, an outlet 103 of a micro-scale size to generate a microjet of the liquid, and an injection part 105 of a micro-scale size connected to the outlet 103 and adapted to be inserted into a skin tissue to a preset depth, and the pressure providing part 200 includes a first pressure applying part 201 connected to the first reservoir part 101 and configured to apply pressure to the liquid, and a first pressure generator 203 to provide the pressure to the first pressure applying part 201.

The nozzle part 100 is configured to eject a microjet injectable into the skin, and includes the first reservoir part 101, the outlet 103, and the injection part 105. Also, according to another exemplary embodiment of the present disclosure, a third pressure applying part 109 which applies the pressure to the first reservoir part 101 may be further included.

According to an exemplary embodiment of the present disclosure, the first reservoir part 101 is configured to store a liquid corresponding to a single dose. The first reservoir part 101 may be connected to a liquid providing part which provides a liquid through a first provision connecting part 107. According to an exemplary embodiment of the present disclosure, a liquid providing part of manual or automated type which provides a preset amount of liquid, for example, a liquid corresponding to a single dose, may be further included. The present disclosure is not necessarily limited thereto, and similar to the previous embodiment, the liquid providing part may be integrally formed with the first reservoir part 101.

According to an exemplary embodiment of the present disclosure, a single dose injectable through the first reservoir part 101 may be from 1 to 1000 µl. The present disclosure is not necessarily limited thereto, and it is obvious that the single dose may be variously selected as desired.

Referring to FIG. 3B, the outlet 103, or orifice may be adapted to have a desired size in diameter to generate a microjet of a desired liquid.

According to an exemplary embodiment of the present disclosure, a jet force of the microjet may be adjusted by adjusting the diameter of the outlet 103. Because the diameter of the outlet 103 is inversely proportional to the jet force of the microjet, the jet force of the microjet may be adjusted by adjusting the diameter of the outlet 103 based on a part and a property of a target skin or tissue.

According to an exemplary embodiment of the present disclosure, a minimum diameter ($t_1$) of the outlet 103 may be less than or equal to 0.5 mm. When the minimum diameter ($t_1$) of the outlet 103 exceeds 0.5 mm, a high speed and high pressure microjet is not generated and is difficult to permeate into a skin to a desired depth.

Also, the minimum diameter ($t_1$) of the outlet 103 may be less than or equal to 0.3 mm, and preferably, may be less than or equal to 0.2 mm. This is to permeate the liquid into a desired skin tissue quickly under pressure within the nozzle part 100.

According to an exemplary embodiment of the present disclosure, an area being jetted may be adjusted. By placing a plurality of outlets 103 and injection parts 105 within an area of a microject of a desired area, it is possible to inject the liquid at a plurality of spots over a wide area rather than one spot on the skin. Thus, according to an exemplary embodiment of the present disclosure, a desired liquid may be injected into a wide area through a single injection, but not multiple injections.

The injection part 105 is configured to inject the liquid filled in the first reservoir part 101 into a target skin tissue. The microjet ejected through the outlet 103 may be guided to a preset skin depth by the desired injection part 105. According to an exemplary embodiment of the present disclosure, a needle of a micro-scale size may be used as the injection part 105.

According to an exemplary embodiment of the present disclosure, before injection, the injection part 105 may come into contact with the skin, penetrate through the stratum corneum or the epidermis, and be located on the dermis. Also, a high speed and high pressure microjet may be ejected into and below the dermis at a high speed, penetrate into a target part, and be diffused and absorbed into a surrounding tissue.

Referring to FIG. 3B, an insertion depth ($t_2$) of the injection part 105 according to an exemplary embodiment of the present disclosure may be from 0.1 to 20 mm. When the insertion depth is less than 0.1 mm, it is difficult to guide through the stratum corneum or the epidermis, and when the insertion depth exceeds 20 mm, an object may feel pain.

Preferably, based on a location and a skin thickness of a target part, the insertion depth ($t_2$) of the injection part 105 may be from 0.5 to 10 mm and from 0.2 to 5 mm.

According to an exemplary embodiment of the present disclosure, an inner diameter ($t_3$) of the injection part 105 may be from 50 to 450 µm. When the inner diameter is less than 50 µm, it is difficult to generate a microjet, and when the inner diameter exceeds 450 µm, a liquid may come out or bleeding may occur.

Preferably, the inner diameter ($t_3$) of the injection part 105 may be from 50 to 410 µm, from 50 to 220 µm, and from 50 to 170 µm, based on properties of a target liquid such as viscosity or a target part.

Referring to FIGS. 3A and 3B, according to an exemplary embodiment of the present disclosure, a third pressure applying part 109 which applies the pressure to the first reservoir part may be further included. The third pressure applying part 109 may be, but not necessarily limited to, a plunger.

The third pressure applying part 109 is connected to the pressure providing part 200, to be concrete, a first pressure applying part 201, and is configured to transmit the pressure provided by the pressure providing part 200 to the first reservoir part 101.

The third pressure applying part 109 may be located at a retracted position in a liquid filling state (see FIG. 3A), and at an extended position in a liquid ejection state (see FIG. 3B). Particularly, according to an exemplary embodiment of the present disclosure, the third pressure applying part 109 may have a protrusion 108 corresponding to the outlet 103. The protrusion 108 may be respectively inserted into the outlet 103, thereby generating a high speed and high pressure microjet more efficiently.

Referring to FIG. 3A, to limit the extended distance of the first pressure applying part 201 or the third pressure applying part 109, a ring 401 is formed in the first pressure applying part 201 and a groove 403 is formed in the first reservoir part 101 at a location corresponding to the extended distance such that the groove 403 may be engaged with the ring 401, and by their coupling, the extended distance may be limited.

Also, referring to FIG. 3C, or a partially enlarged view of the nozzle part 100 according to another exemplary embodiment of the present disclosure, a locking step 405 connected to a spring is formed on the third pressure applying part 109, and the locking step 405 may be adapted to be engaged with a groove part 407 formed at a location corresponding to the extended distance or the first provision connecting part 107.

Figure 4:
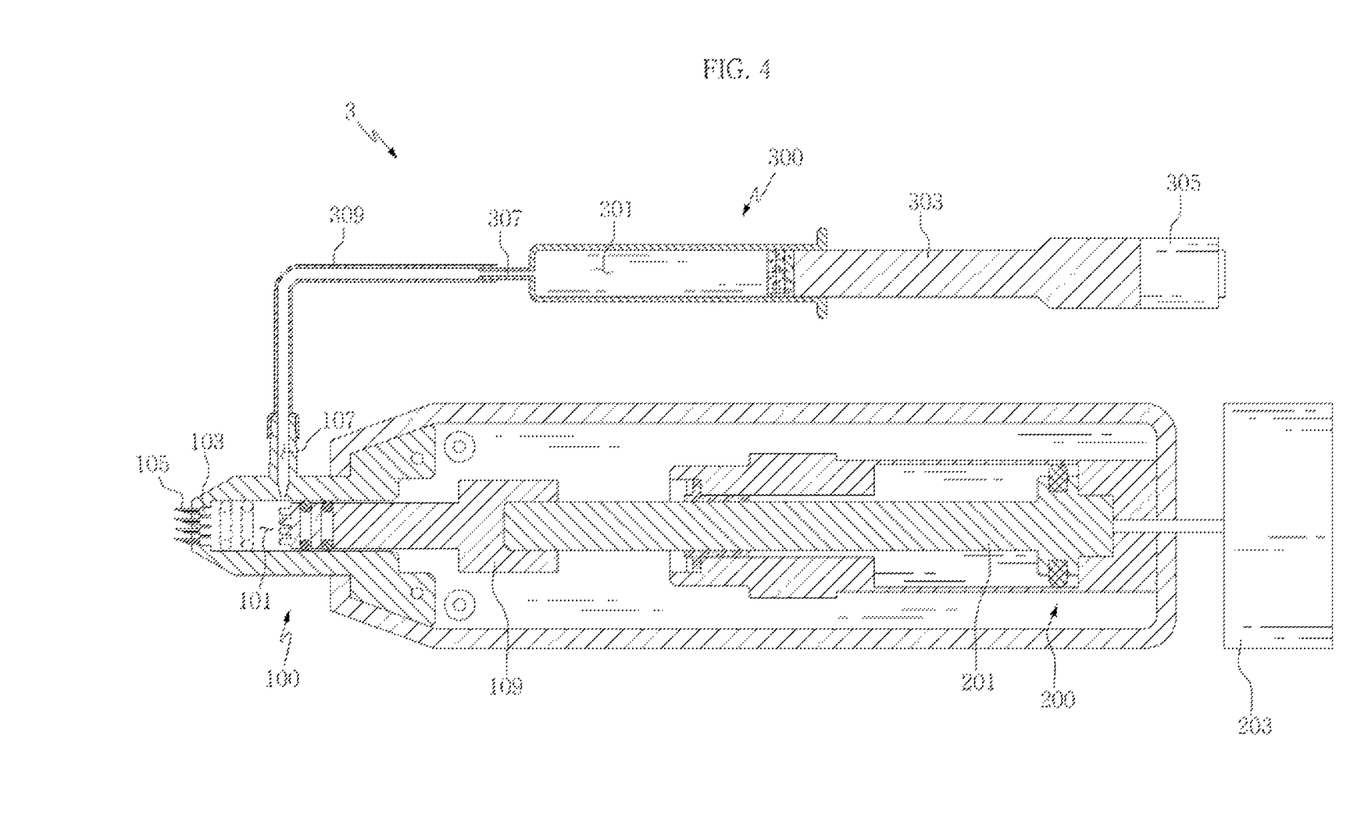
FIG. 4 is a schematic diagram illustrating a minimally invasive injection device according to a third exemplary embodiment of the present disclosure.

Referring to FIGS. 2 and 4, the pressure providing part 200 is configured to provide the pressure to allow the nozzle part 100 to generate a microjet.

The pressure providing part 200 includes the first pressure applying part 201 and the first pressure generator 203.

The first pressure applying part 201 may be a piston adapted to make a linear motion within the pressure providing part 200 or a housing of the minimally invasive injection device.

The first pressure generator 203 corresponds to a device for providing the pressure to the first pressure applying part 201, and may be configured to provide the pressure by various methods in the art, for example, a motor type, an air pressure type, or a gas emission type.

The first pressure generator 203 enables the first pressure applying part 201 to make an instantaneous high-speed linear motion, and when the first pressure applying part 201 moves forward instantaneously at a high speed within the pressure providing part 200, the pressure may be applied to the liquid present in the first reservoir part 101 of the nozzle part 100 directly through the first pressure applying part 201 or indirectly through the third pressure applying part 109.

According to an exemplary embodiment of the present disclosure, the first pressure generator 203 may further include a controller (not shown) to control at least one of a magnitude and a generation time of the pressure generated by the first pressure generator 203. That is, the controller is configured to allow a user to adjust an amount of energy generated by the first pressure generator 203 through the controller, and particularly, the controller is configured to adjust a permeation depth of the microjet, for example, to a depth sufficient for the microjet to permeate into and below the dermis by adjusting the strength of the pressure, and adjust a jet amount by adjusting the pressure generation time.

According to another exemplary embodiment of the present disclosure, the first pressure generator 203 may be configured to control the extended distance or the retracted distance of the first pressure applying part 201 by the controller.

The extended distance of the first pressure applying part 201 corresponds to a single dose, and the retracted distance of the first pressure applying part 201 is proportional to an amount of liquid stored in the first reservoir part 101.

According to an exemplary embodiment of the present disclosure, the amount of liquid stored in the first reservoir part 101 may be adjusted by controlling the retracted distance of the first pressure applying part 201. For example, to store a single dose in the first reservoir part 101, an amount of liquid corresponding to a single dose may be stored in the first reservoir part 101 by moving the first pressure applying part 201 backward.

To store a single dose of liquid in the first reservoir part 101, the liquid may be stored using a liquid providing part 300 of automated or manual type by adjusting the retracted distance of the first pressure applying part 201 or the third pressure applying part 109, or by adjusting the retracted distance of the first pressure applying part 201 through the controller in such a state that the first reservoir part 101 is connected to a liquid supply source (not shown).

According to an exemplary embodiment of the present disclosure, it is obvious that a transparent window through which a storage amount of the first reservoir part 101 is seen may be configured to observe an amount of liquid being injected.

According to an exemplary embodiment of the present disclosure, the controller may be connected to the first pressure generator 203 and configured to enable the first pressure applying part 201 to continuously move forward or repeatedly move forward and backward.

That is, the microjet may be continuously ejected by a continuous forward movement of the first pressure applying part 201, and when a single dose of liquid is stored in the first reservoir part 101, the microjet may be continuously ejected automatically by performing a one-time ejection and a one-time storage automatically through continuous forward and backward movements of the first pressure applying part 201, while being connected to the liquid supply source.

Thus, according to an exemplary embodiment of the present disclosure, the minimally invasive injection device may continuously inject a liquid without separately performing inflow and ejection operations of the liquid. Accordingly, a user's effort to inject a liquid each time may reduce.

According to an exemplary embodiment of the present disclosure, the first pressure generator may include, but not necessarily limited to, any one of the group consisting of a compression spring, compressed gas, an explosive chemical substance, piezoelectricity, an electric driving motor, a linear Lorentz's force driving motor, an electric cylinder, and a linear motion guide, and various pressure generators in the art may be applied.

According to an exemplary embodiment of the present disclosure, the first pressure generator 203 may be configured to generate the pressure from 1 to 100 bar. When the pressure less than 1 bar is generated, it is difficult to generate a microjet, and when the pressure higher than 100 bar is generated, an unwanted damage may occur to an object.

FIG. 4 is a cross-sectional view illustrating a minimally invasive injection device 2 according to a third exemplary embodiment of the present disclosure, including the nozzle part 100, the pressure providing part 200, and a liquid providing part 300.

According to an exemplary embodiment of the present disclosure, the nozzle part 100 may be configured to provide the liquid to the first reservoir part 101 by connecting a tube to the first provision connecting part 109 or directly connecting to a liquid supply source or the liquid providing part 300 of automated or manual type.

According to an exemplary embodiment of the present disclosure, when the liquid is provided while being connected to the liquid supply source as described in the foregoing, or a single dose or more is stored in the first reservoir part 101, the liquid may be ejected by forward and backward movements of the first pressure applying part 201 of the pressure providing part 200.

Also, when the liquid providing part of manual type is used, the liquid may be provided to the first reservoir part 101 by connecting a device such as a general syringe including a piston to the first provision connecting part 107 directly or indirectly through a tube.

Also, according to the exemplary embodiment of FIG. 4, when the liquid providing part 300 of automated type is used, the liquid providing part 300 may include a second reservoir part 301 to store the liquid to be injected, a second pressure applying part 303 to apply the pressure to the second reservoir part 301, and a second pressure generator 305 to provide the pressure to the second pressure applying part.

According to an exemplary embodiment of the present disclosure, a second provision connecting part 307 may be connected to the first provision connecting part 107 by a tube 309, and the second reservoir part 301 serves to store the liquid and provide the liquid of a preset amount, for example, the liquid corresponding to a single dose to the first reservoir part 101.

The liquid providing part 300 may be provided with the second pressure applying part 303 to apply the pressure to the second reservoir part 301, and according to an exemplary embodiment of the present disclosure, the second pressure applying part 303 may include a piston, or a flow rod connected to the piston to induce a linear motion of the piston.

Also, the liquid providing part 300 may include the second pressure generator 305 to provide the pressure to the second pressure applying part 303 to cause a linear motion. An amount of liquid being provided to the first reservoir part 101 may be determined based on a movement distance of the second pressure applying part 303 by the second pressure generator 305.

According to an exemplary embodiment of the present disclosure, a controller (not shown) which is connected to the second pressure generator 305 and configured to control a movement distance of the second pressure applying part 303 by the second pressure generator 305 to adjust a single dose may be further included. The controller of the second pressure generator 305 may be the same as the controller of the first pressure generator 203, and the second pressure generator 305 may be controlled by a separate controller.

The second pressure generator 305 may be any one of the group consisting of a compression spring, compressed gas, an explosive chemical substance, piezoelectricity, an electric driving motor, a linear Lorentz's force driving motor, an electric cylinder, and a linear motion guide, but the present disclosure is not necessarily limited thereto, and various pressure generators in the art may be used.

According to an exemplary embodiment of the present disclosure, the second pressure generator 305 may be configured to generate the pressure from 1 to 100 bar, but the present disclosure is not necessarily limited thereto.

According to an exemplary embodiment of the present disclosure, the first pressure generator 203 and the second pressure generator 305 may be formed as an integral pressure generator and connected to the first pressure applying part 201 and the second pressure applying part 303, respectively, but the present disclosure is not necessarily limited thereto, and it is obvious that the first pressure generator 203 and the second pressure generator 305 may be separately formed.

The liquid may include, but not necessarily limited to, at least one selected from the group consisting of hyaluronic acid, collagen, a stem cell, a stem cell culture fluid, a fat cell, fat, silicon, vitamin, a placenta extract, blood plasma, tranexamic acid, a saline solution, polyvinyl alcohol, poly (methyl methacrylate), polyethylene glycol, cross-linked hyaluronic acid, calcium hydroxy apatide, polylactic acid (PLLA), poly(lactic-co-glycolic acid) (PLGA), pteroylglutamic acid (PGA), poly-gamma-glutamic acid, phospholipid, deoxycholic acid, minoxidil, finasteride, dutasteride, a growth factor, botulinum toxin, alginic acid, chitosan, chondroitin sulfate, dermatan sulfate, hyaluronate lyase, an antibody, a pain relief ingredient, and an anesthetic ingredient, and may include various substances used in the art.

The liquid may be provided in at least one type of a solution, a suspension, and a dispersion in which particles including active ingredients are dispersed, but the present disclosure is not necessarily limited thereto, and the liquid may be provided in various states available in the art.

Figure 5:
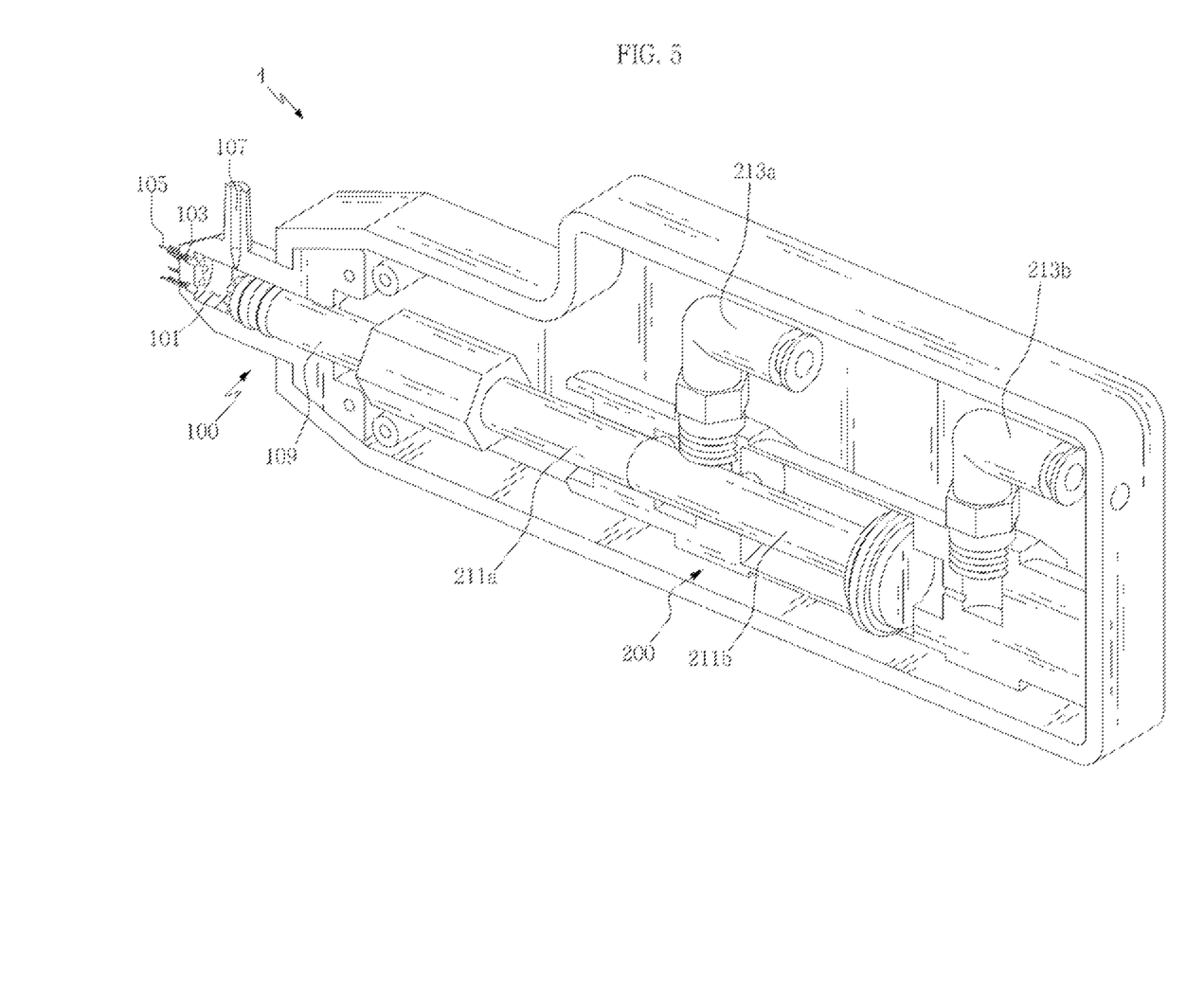
FIG. 5 is a cross-sectional view illustrating a minimally invasive injection device according to a fourth exemplary embodiment of the present disclosure.

FIG. 5 is a cross-sectional view illustrating a minimally invasive injection device 4 according to a fourth exemplary embodiment of the present disclosure.

Referring to FIG. 5, the minimally invasive injection device 4 includes the nozzle part 100 and the pressure providing part 200.

The nozzle part 100 of the minimally invasive injection device 4 according to the fourth exemplary embodiment of the present disclosure includes the first reservoir part 101, the outlet 103, and the injection part 105 connected to the outlet 103, and the third pressure applying part 109 is provided in the first reservoir part 101 to apply pressure to the first reservoir part 101. Also, the first reservoir part 101 is equipped with the first provision connecting part 107 to provide a liquid using a liquid supply source or a pressure providing part of manual or automated type.

The pressure providing part 200 includes a first pressure applying part which makes a linear motion and is connected to the third pressure applying part 109. The first pressure applying part may be constructed as a series of connecting rods 211a and 211b to transmit the pressure to the third pressure applying part 109.

The connecting rods 211a and 211b according to the fourth exemplary embodiment of the present disclosure are connected to a first pressure generator (not shown) and adapted to make a linear reciprocating motion, and specifically, the first pressure generator (not shown) may be configured to allow air inflow or outflow to two air providing parts 213a and 213b to move the connecting rods 211a and 211b forward at a high speed.

Figure 6:
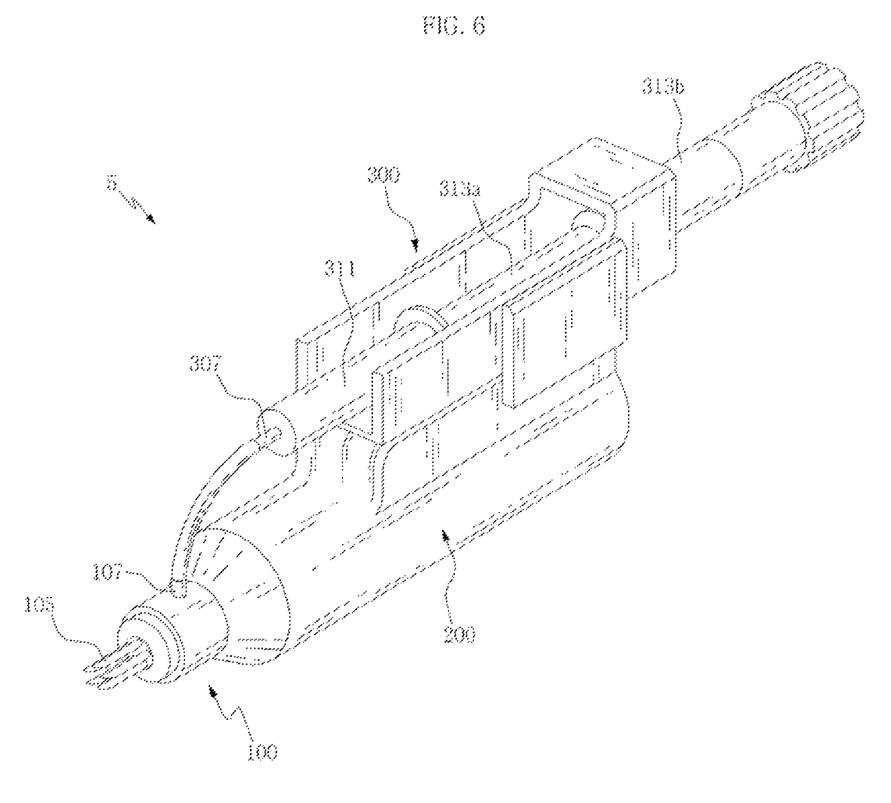
FIG. 6 is a perspective view illustrating a minimally invasive injection device according to a fifth exemplary embodiment of the present disclosure.

FIG. 6 is a perspective view illustrating a minimally invasive injection device 5 according to a fifth exemplary embodiment of the present disclosure.

Referring to FIG. 6, the minimally invasive injection device 5 according to the fifth exemplary embodiment of the present disclosure includes the nozzle part 100, the pressure providing part 200, and the liquid providing part 300. According to the fifth exemplary embodiment of the present disclosure, the nozzle part 100, the pressure providing part 200, and the liquid providing part 300 are provided as mounted in a housing, and the integral minimally invasive injection device 5 may provide convenience in portability and manipulation to a user.

The nozzle part 100 of the minimally invasive injection device 5 according to the fifth exemplary embodiment of the present disclosure includes the first reservoir part, the outlet, and the injection part 105 connected to the outlet, and the third pressure applying part is provided in the first reservoir part to apply pressure to the first reservoir part. Also, the first reservoir part may be equipped with the first provision connecting part 107 connected to the second provision connecting part 307 to receive a liquid from the liquid providing part 300 of automated type.

The pressure providing part 200 may be configured to provide pressure to the nozzle part 100 to thus eject a microjet from the nozzle part 100. According to an exemplary embodiment of the present disclosure, because the plurality of injection parts 105 and outlets 103 are provided within a preset area, a plurality of microjets may be generated within a desired area at once, and consequently, the liquid may be ejected within the desired area at once.

Also, the nozzle part 100 may be connected to the liquid providing part 300 of automated type, and the liquid providing part 300 may include a second reservoir part 311 and a second pressure applying part including a series of flow rods 313a and 313b which applies pressure to the second reservoir part 311. Also, the second pressure applying part may be connected to a second pressure generator (not shown) which operates by various mechanisms such as a motor type or a hydraulic type to provide pressure causing a linear reciprocating motion.

According to an exemplary embodiment of the present disclosure, there is provided a minimally invasive injection device which may perform supply and injection of a liquid by a series of automated operations and stably provide a liquid to a target location below the epidermis.

According to an exemplary embodiment of the present disclosure, there is provided a minimally invasive injection device which may inject a liquid to a desired target depth independent of properties of an active substance to be administered, that is, the liquid. Particularly, in the case of a high viscosity liquid, phenomena occurs in which the liquid does not penetrate the stratum corneum or the epidermis of the skin due to the high viscosity or a jet of sufficient velocity is not generated and the jet is not diffused into the skin quickly and comes out of the skin, but the minimally invasive injection device of the present disclosure guides a microjet to a minimum depth using the injection part and ejects the microjet, and thus allows an active substance to be absorbed to a target depth without an outflow phenomenon.

Also, according to an exemplary embodiment of the present disclosure, there is provided a minimally invasive injection device which may minimize pain or bleeding of an object, avoid creating a large needle hole and consequently keep an administered liquid from flowing back out, and prevent a liquid loss caused by a liquid outflow, resulting in improved permeation capability and efficiency.

INDUSTRIAL APPLICABILITY

There is provided a nozzle device which may alleviate discomfort of a patient caused by pain and bleeding while minimizing an injection loss ratio under a skin when a microjet is permeated through the skin and a minimally invasive injection device. Also, there is provided a nozzle device which may deliver a uniform amount of liquid to a uniform depth independent of skin characteristics of an individual when injecting a liquid including active ingredients of various properties and a minimally invasive injection device.

What is claimed is:

1. A minimally invasive injection device, comprising:
   a nozzle part comprising a first reservoir part to contain a liquid to be injected, an outlet to generate a microjet of the liquid, and an injection part of a micro-scale size connected to the outlet and adapted to be penetrated and inserted into stratum corneum or epidermis so that the liquid is injected into and below the dermis by the microjet; and
   a pressure providing part comprising a first pressure applying part, a third pressure applying part connected to the first pressure applying part and configured to apply the pressure to the first reservoir part, and a first pressure generator to provide the pressure to the first pressure applying part, wherein a plurality of outlets and injection parts connected thereto are connected to the first reservoir part, and a plurality of protrusions corresponding to the outlets are formed in the third pressure applying part, and wherein a ring or a locking step is formed in the third pressure applying part and a groove engaged with the ring of a groove part engaged with the locking step is formed in the reservoir part at a location corresponding to an extended distance.

2. The minimally invasive injection device according to claim 1, further comprising:
   a liquid providing part of manual or automated type connected to the first reservoir part and configured to provide the liquid of a preset amount.

3. The minimally invasive injection device according to claim 1, wherein a single dose ejectable from the first reservoir part is from 1 to 1000 μl.

4. The minimally invasive injection device according to claim 2, wherein the liquid providing part of automated type comprises a second reservoir part to store the liquid to be injected, a second pressure applying part to apply pressure to the second reservoir part, and a second pressure generator to provide the pressure to the second pressure applying part.

5. The minimally invasive injection device according to claim 4, further comprising:
   a controller connected to the second pressure generator and configured to control a movement distance of the second pressure generator.

6. The minimally invasive injection device according to claim 1, further comprising:
   a controller connected to the first pressure generator and configured to control at least one of a magnitude and a generation time of the pressure generated by the first pressure generator.

7. The minimally invasive injection device according to claim 6, wherein the controller is connected to the first pressure generator and configured to control an extended distance or a retracted distance of the first pressure applying part.

8. The minimally invasive injection device according to claim 6, wherein the controller is connected to the first pressure generator and configured to control to continuously move the first pressure applying part forward or repeatedly move the first pressure applying part forward and backward.

9. The minimally invasive injection device according to claim 1, wherein a jet force of the microject being jet is adjusted by adjusting a diameter of the outlet.

10. The minimally invasive injection device according to claim 4, wherein the first pressure generator or the second pressure generator includes at least one of the group consisting of a compression spring, compressed gas, an explosive chemical substance, piezoelectricity, an electric driving motor, a linear Lorentz's force driving motor, an electric cylinder, and a linear motion guide.

11. The minimally invasive injection device according to claim 4, wherein the first pressure generator and the second pressure generator are an integral pressure generator connected to the first pressure applying part and the second pressure applying part.

12. The minimally invasive injection device according to claim 1, wherein an area in which the plurality of outlets and injection parts connected to the outlets are placed is adjusted to adjust an ejection area of the microjet.

13. The minimally invasive injection device according to claim 4, wherein the first pressure generator or the second pressure generator is adapted to generate the pressure from 1 to 100 bar.

* * * * *